United States Patent [19]

Solow

[11] 4,346,492

[45] Aug. 31, 1982

[54] MECHANICAL TOOTHBRUSH WITH INDIVIDUAL TUFT DRIVE

[76] Inventor: Terry S. Solow, 410 Playa Blvd., La Selva Beach, Calif. 95076

[21] Appl. No.: 128,629

[22] Filed: Mar. 10, 1980

Related U.S. Application Data

[63] Continuation-in-part of Ser. No. 965,055, Nov. 30, 1978, Pat. No. 4,224,710.

[51] Int. Cl.³ ............................................. A46B 13/02
[52] U.S. Cl. ................................. 15/22 R; 128/62 A
[58] Field of Search .................. 15/22 R, 22 A, 22 C, 15/167 A, 201, 371, 21 R, 21 B; 128/53, 62 A

[56] References Cited

U.S. PATENT DOCUMENTS

| | | | |
|---|---|---|---|
| 2,882,544 | 4/1959 | Hadidian | 15/167 |
| 2,935,755 | 5/1960 | Leira et al. | 15/167 |
| 3,683,442 | 8/1972 | Holly | 15/167 |
| 4,223,417 | 9/1980 | Solow | 15/22 R |

FOREIGN PATENT DOCUMENTS 2255671  5/1973  Fed. Rep. of Germany ........ 15/167

*Primary Examiner*—Edward L. Roberts
*Attorney, Agent, or Firm*—Robert G. Slick

[57] ABSTRACT

A power actuated toothbrush is provided wherein the brush consists of a plurality of tufts which are individually driven by means whereby the tufts are forced to move coaxially back and forth against the teeth to give a jackhammer-type action. The tufts may be driven mechanically, or by a fluid drive, preferably pneumatic. The tufts automatically adapt for irregularities in the teeth and gums and enter the sulcus and embrasures for thorough cleaning.

8 Claims, 10 Drawing Figures

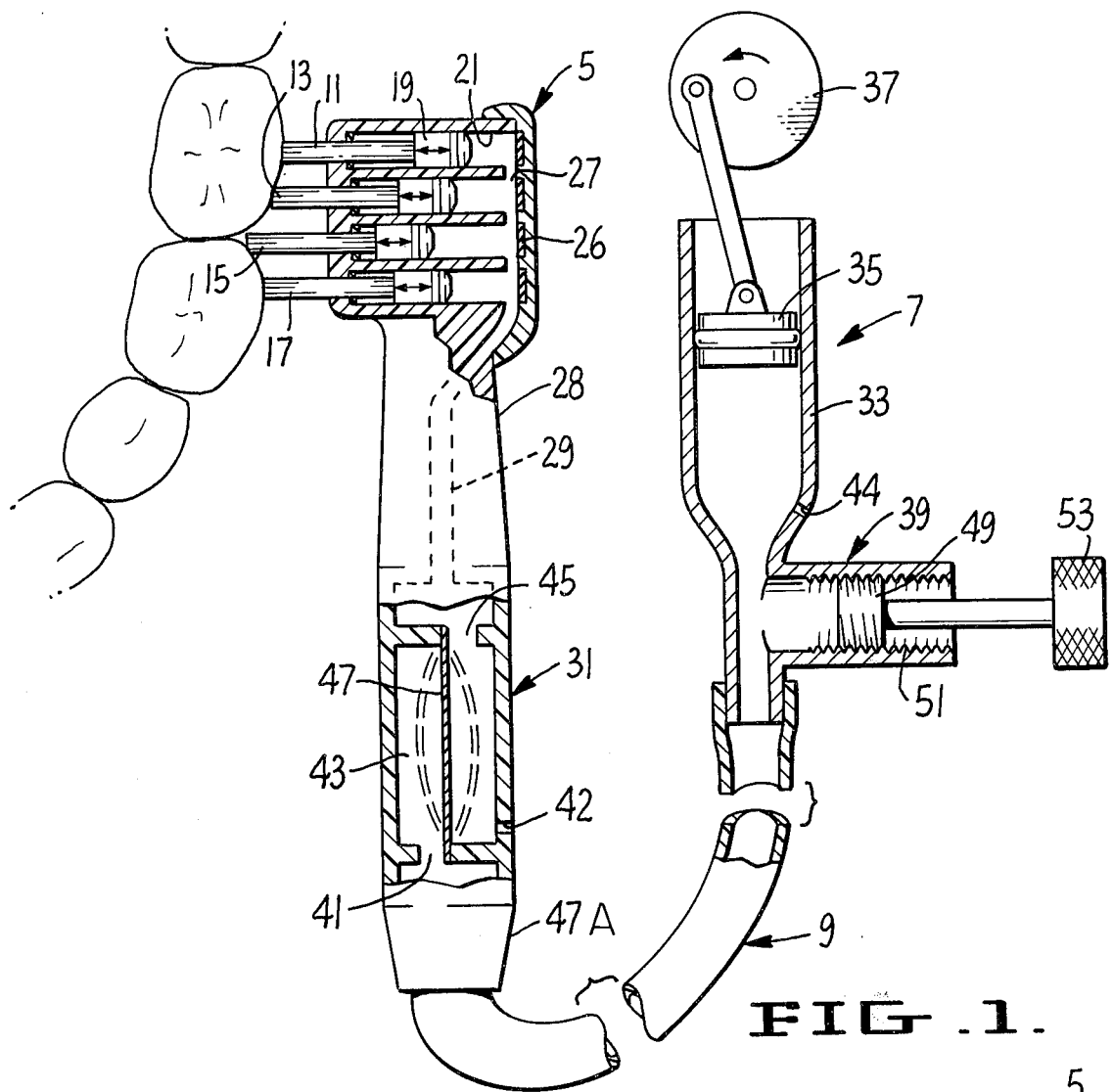
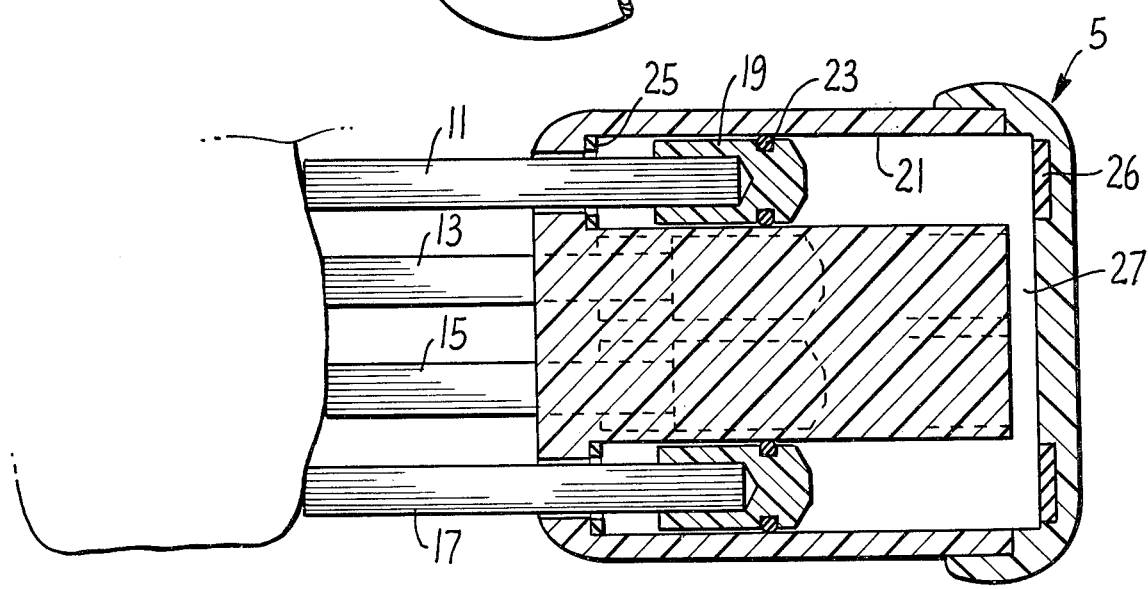

MECHANICAL TOOTHBRUSH WITH INDIVIDUAL TUFT DRIVE

REFERENCE TO RELATED APPLICATION

This application is a continuation in part of my application Ser. No. 965,055 filed Nov. 30, 1978, now Pat. No. 4,224,710.

SUMMARY OF THE INVENTION

Ordinary mechanical toothbrushes have a brush head with a plurality of tufts therein, wherein the entire head is driven in an orbital, circular or brushing motion. With such a brush, the motion is limited to a large degree by the nearest object which the bristles contact. For example, if the brush hits the side of a tooth, bristles will not readily enter depressed areas or irregularities such as the embrasures and gaps caused by crooked teeth.

Accordingly, it is a broad object of the present invention to provide a toothbrush wherein the head consists of a plurality of individual tufts that are attached to pistons which are driven by a gas or a liquid, in a reciprocating manner whereby the movement of one tuft is not inhibited by the restraint which might be placed on an adjacent tuft as in a regular stiff-backed brush, so that each of the tufts is brought to bear against an irregular surface with substantially equal pressure. Preferably, the drive is accomplished by the use of air in a pressure-suction reciprocating mode, although other fluids, such as water, may be employed.

In accordance with one embodiment of the invention, an air and/or moisture trap is provided in or near the head, so that a plurality of people can use their individual brush heads with a common driving unit, without fear of spreading germs from one user to the next. This trap is a back-up system if a piston O-ring should malfunction and leak.

In accordance with the preferred embodiment of the invention, the bristles are driven by alternate suction and pressure exerted within the brush head and, in accordance with another embodiment of the invention, the bristles are driven against the teeth by short bursts of pressure, and a spring is employed to return the tuft to its retracted position. The latter pressure-only system where vacuum is not employed is leakproof, so that a trap is not required.

In accordance with another embodiment of the invention, two or more brush heads can be employed, with these brush heads set at an angle to each other so that more than one surface of a tooth can be cleaned at the same time.

In accordance with still another embodiment of the invention, the pistons are deliberately allowed to leak and a simple flushing system is provided wherein water is pumped through the head, past the pistons and out over the bristles to clean the interior of the brush as well as the bristles. This can be followed by pumping air through the chamber to dry it out. Also, in this embodiment of the invention, the bristles are always left in an extended position so that they will be out in the air for drying.

The tufts may be driven in any selected phase relationship with one another. For example, alternate rows of tufts could be driven 180° C. out of phase with each other in order to reduce residual vibration. This could be accomplished with two separate drivers and a hose and handle, each with two channels.

Various other additional features and advantages of the invention will be brought out in the balance of the specifications.

BRIEF DESCRIPTION OF THE DRAWINGS

FIG. 1 is a side view, partly in section, of a toothbrush and drive mechanism embodying my invention.

FIG. 2 is an enlarged section of the brush head showing a plurality of tufts.

DESCRIPTION OF THE PREFERRED EMBODIMENTS

Figure 3:
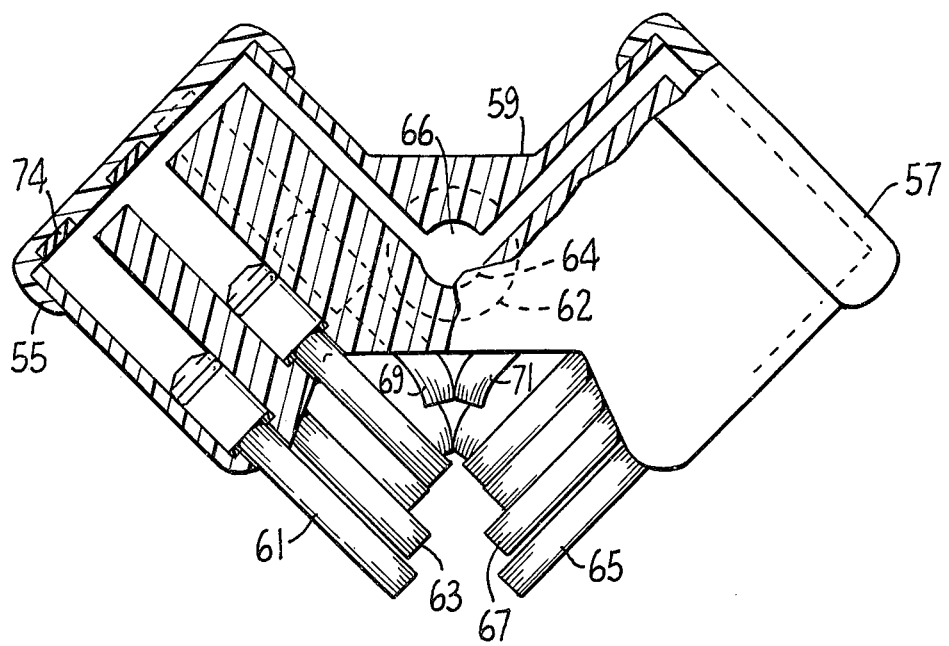
FIG. 3 is a end view, partly in section, showing an embodiment of my invention wherein more than one head is employed.

Referring now to the drawings by reference characters, there is shown in FIGS. 1 and 2 a brush head, generally designated 5, and a drive mechanism, generally designated 7. The brush mechanism 5 and the drive mechanism 7 are connected together by a length of hollow, flexible tubing 9.

In the brush head 5, for simplicity and clarity, only one row of four tufts, designated 11, 13, 15 and 17, is shown. It will be realized that normally a larger number of tufts is employed and these tufts generally are configured to form several additional rows staggered from side to side. Each of these tufts, which may contain any selected number of bristles, is secured to a piston. For example tuft 11 is secured to piston 19 and so on. Piston 19 is adapted for reciprocation within cylinder 21 and is provided with a sealing O-ring 23. 25 is an O-ring-shaped rubber bumper while 26 is a disc-shaped rubber bumper. These bumpers absorb the piston impact on each end of its reciprocating excursion. Each of the cylinders is connected to a common chamber 27, connected to a passage 29 in a handle 28 which is connected to the hollow, flexible tube 9. In the embodiment shown in FIG. 1, the handle 28 is provided with a diaphragm or trap device 31, which may or may not be used and which is later described in detail.

Tube 9 leads to a cylinder 33 in which a piston 35 is adapted to reciprocate by means of the crank mechanism 37. Near the bottom of the cylinder 33 is a volume adjustment mechanism 39 which may or may not be used and which is later described in detail.

As the piston 35 is caused to reciprocate, the pressure of the fluid in the device will increase and then decrease in an oscillatory manner, above and below atmospheric pressure. This will cause the pistons located in the brush head, and thus the tufts 11, 13, 15 and 17, to reciprocate so that they are given a jackhammer action against the sides of the tooth. It is also apparent, that the tufts will not reciprocate as a unit but instead will individually "bottom out" when they strike an object. Thus, referring specifically to FIG. 1, it is seen that tuft 11 has struck the side of a tooth very close to the head while tuft 15 has entered the embrasure between two teeth and thus is extended out much further. It is also apparent that the action is entirely different from that which would be achieved by a brush having tufts embedded in a stiff back, even if this stiff-backed brush was caused to move back and forth in relation to the tooth. Thus, if all the tufts were moved as a unit as in the usual stiff-backed brush, tuft 11 would ordinarily stop the action when it contacted the tooth so that a tuft such as 15 would not serve a useful function. However, if excessive force were employed to try to make tuft 15 enter the deep embrasure, the other tufts, such as 11, 13 and 17, would be bent askew and distorted so that their bristle ends would not contact and clean the teeth and gums. In addition, this excessive force might damage sensitive gums.

With such a mechanical toothbrush, a number of members of a family might have individual brush heads and use a common drive mechanism. With the mechanism described, there is a remote possibility that a slight amount of liquid from the mouth might be drawn into the drive mechanism because of an O-ring seal malfunction, producing an unsanitary condition if the device were used by several people. For extra insurance, the diaphragm arrangement, generally designated 31, may be built into the handle 28. Although this can take several forms, a simple mechanism is shown wherein a first passage 41 leads to one side of a chamber 43 and a second passage 45 leads to the other side of the chamber. A flexible diaphragm or bladder 47 is employed to divide the chamber 43 into two sections so that as the pressure alternates in tube 9, diaphragm 47 is caused to alternate, as is shown by the dashed lines. Thus, pressure-suction is transmitted through the passage 45 and tube 29, yet there is no actual fluid communication between the tube 29 and the tube 9. In effect, this provides a hermetic seal. Normally with such an arrangement, a snap-on connector 47A is employed to facilitate changing heads quickly and easily. Pin holes 42 and 44 serve as integrators and equalize pressure under long term conditions but are so small in size that they do not interfere with normal operation.

The system shown in FIG. 1 is a closed system and one can regulate the force exercised by the brushes by regulating the volume of the system. For this purpose, the adjustor 39 may be employed which consists merely of a tightly fitted, threaded piston 49 which can move back and forth within the threaded cylinder 51. An adjusting handle 53 is provided so that one can easily change the volume, and thus the pressure within the system, merely by turning the handle 53.

In some instances, two or even more brush heads can be employed advantageously. Such an arrangement is shown in FIG. 3 where two heads 55 and 57 are set at substantially right angles to each other and held by the center member 59. The heads have a plurality of tufts such as those designated 61 and 63, and so on in head 55 and those designated 65 and 67, and so on in head 57. A common air passage 66 delivers pressure and/or suction to all of the pistons, driving the individual tufts as previously described.

Figure 5:
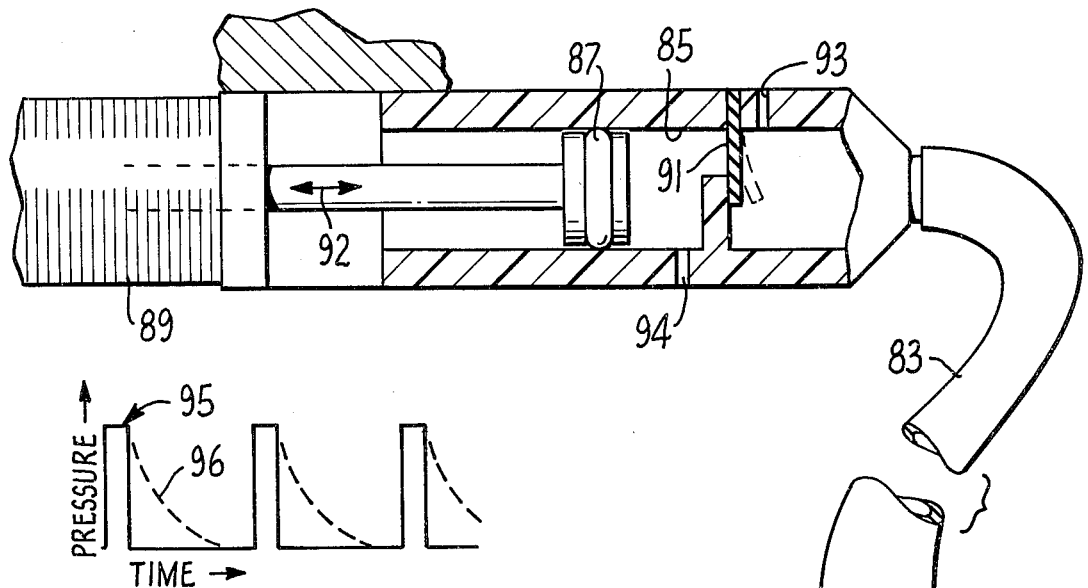
FIG. 5 is a graph showing the relationship of pressure versus time of the air within the device shown in FIG. 4.
Figure 4:
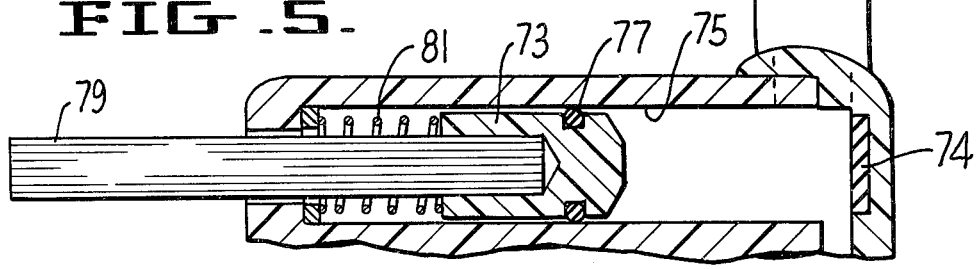
FIG. 4 is a view, partly in section, showing another embodiment of my invention wherein a pressure drive and spring returna re used for the individual tufts.

Although it is preferred to actuate the individual tufts by alternate pressure and suction means, to avoid any chance of leakage, a pressure-only system (no suction) will be described: With a pressure-only system, a leak cannot contaminate, since no mouth fluids can enter the pressurized system. A spring return can be used whereby it is only necessary to supply short bursts of pressure to the brush heads. This is illustrated in FIG. 4 wherein the piston 73 reciprocates in the cylinder 75, the piston being provided with a sealing O-ring 77. A tuft of one or more bristles 79 is anchored to the piston as previously described. A compression spring 81 is employed within the cylinder to keep the piston and, therefore, the tuft 79 in a normally retracted position. The cylinder 75 is connected to a drive mechanism by means of a tube 83. The drive mechanism consists of a cylinder 85 having a piston 87 therein which can be driven in and out 92 by means of a solenoid 89. Using pneumatic operation as an example, a flapper valve 91 permits air to move only to the right in the cylinder and there are small openings 93 and 94 on each side of valve 91. The spring would normally hold the tuft 79 to the right and as the solenoid 89 is actuated, a short burst of air pressure is produced within the tube 83, causing the flapper valve 91 to deflect momentarily as is shown by the dashed line. Passages 93 and 94 are too small to permit the escape of a substantial amount of air because of the sudden rise of pressure so that piston 73 is driven to the left. After making the stroke, pressure slowly bleeds out through the opening 93 so that the spring 81 can return the tuft 79 to its retracted position for a repetition of the operation. This action is illustrated in FIG. 5 wherein pressure is plotted against time. Thus, there is a sharp rise in pressure at 95, followed by a slow decay 96, followed by a repetition of the cycle.

In the embodiments of the invention heretofore described, the pistons have been provided with sealing O-rings so that a hermetic seal is provided, preventing the entrance of moisture into the interior of the brush head. In the embodiment of the invention illustrated in FIGS. 6 through 10, pistons are employed that use no sealing O-rings. This approach reduces friction, lowers manufacturing costs and increases reliability. In effect, the pistons are deliberately allowed to leak a small amount. With this minor leak, the pneumatic drive efficiency is not seriously affected. In addition, any mouth fluid leakage past the pistons into the head and handle cannot go past the diaphragm. During flushing, this internal area is thoroughly rinsed clean with fresh tap water. This is accomplished by forcing water over the diaphragm, down through the hollow handle, past the pistons and out over the bristles.

It will be noted that during either brushing or flushing, the hose that connects to the handle is never contaminated, because the diaphragm acts as a hermetic seal.

Figure 6:
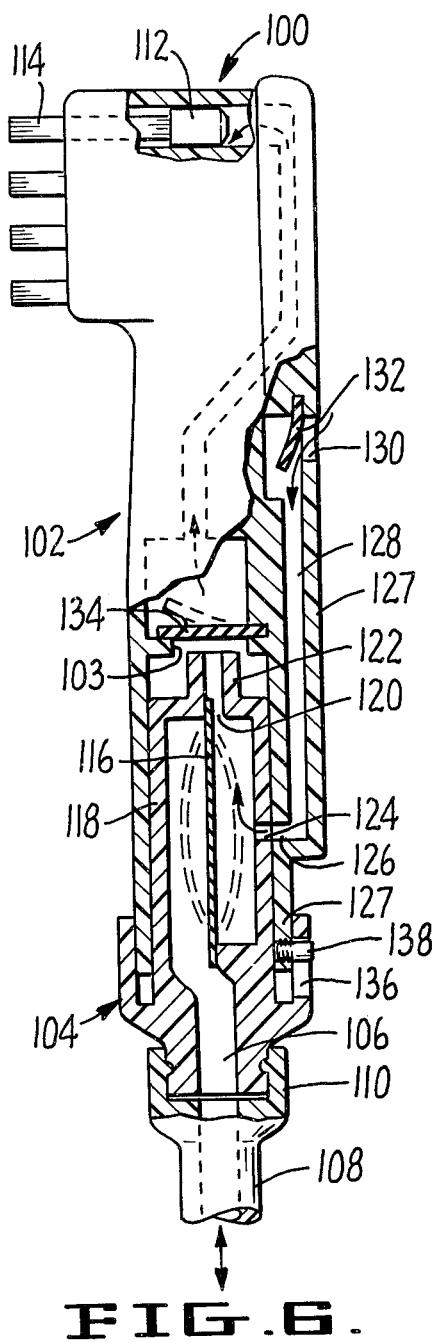
FIG. 6 is a side view, partly in section, of another embodiment of my invention showing the parts in position when the brush is to be flushed.

Referring now to FIG. 6, a brush head 100 is held on a handle 102 and at the rear thereof a handle cover 104 is provided. The handle cover has a passage 106 therein and this is connected to the hollow tube 108 by means of a snap-on connector 110, so that the entire head and handle assembly can be easily attached or detached from tube 108. Thus, a number of the members of a family, each with his own brush assembly, can use the same drive mechanism without fear of cross contamination. Tube 108 leads to a pressure-suction drive mechanism, as previously described in detail. The handle in this embodiment includes an outer wall 127 defining a passage 128.

Head 100 contains a plurality of pistons generally designated 112, each of which is connected to a tuft of bristles 114 as previously described. No attempt is made to have the piston 112 make a perfect seal with the cylinder wall, but instead, a small amount of leakage is tolerated and advantage is taken of this slight leakage around the piston, as will be brought out hereafter.

Figure 7:
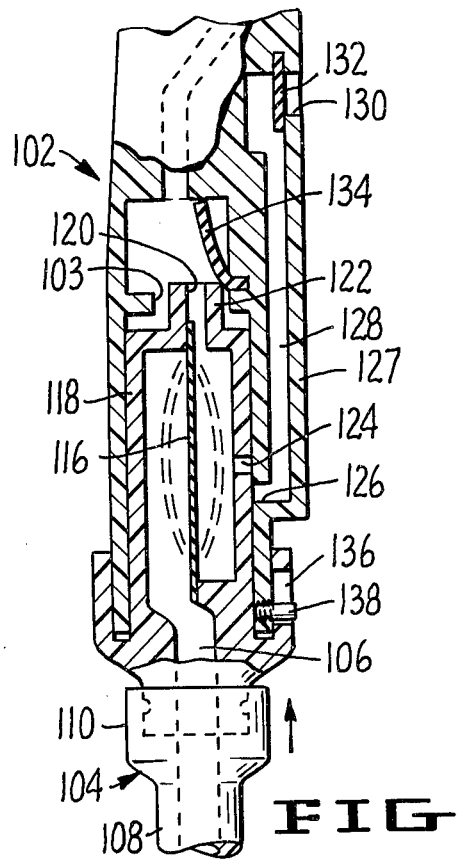
FIG. 7 is a partial view of the structure shown in FIG. 6 with the parts shown in the brushing position.

The handle is provided with a diaphragm 116 but instead of being mounted directly in the handle, the diaphragm is mounted within a chamber 118 which is adapted to slide within the handle and which is attached to or forms part of the handle cover 104. One side of the chamber opens into the passage 106 as shown while the outlet 120 is provided with a projecting tube 122, the purpose of which will later be described. A second passage 124 is provided on the outlet side of the diaphragm and this opens into a passage 126 when the parts are in the flushing position, i.e. the position shown in FIG. 6. Passage 126 leads to a passage 128 and this, in turn, leads to the opening 130 in the exterior of the brush head. The opening 130 is normally closed by a check valve 132. On the interior of the brush, there is a second check valve 134, it being understood that the check valves 132 and 134 are biased in such a manner that they keep the corresponding passages normally closed and permit fluid flow only in through the passage 130 and out through the passage 103. The top of the handle cover is provided with an elongated slot 136 and a screw 138 extends down through this slot into the outer wall 127. It will be apparent that the screw 138 provides an easy method of assembling the structure and, also, the length of the slot 136 limits the back-and-forth movement of the handle cover with respect to the handle and defines the flushing and brushing positions. With the parts in the position shown in FIG. 6, one can now hold the head 100 under a water tap and the diaphragm 116 will act as a pump, sucking water through the opening 130, through the passage 128 down through the passages 126 and 124, over the top of the diaphragm 116 and out through the opening 120, past the check valve 134, thence past the pistons and over the bristles where it is discharged. Thus, with the parts in this position, one can hold the brush head under a water tap and clean fresh water will be drawn through the brush head and discharged along the bristles, cleaning both the interior structure of the brush and the bristles themselves. Now, one withdraws the brush head from the water tap and air will be drawn through the passage 130, effectively drying out the interior of the brush as well as helping to dry the bristles. Further, with this structure, it is apparent that the bristles will always be left in the extended position when power is shut off, and not in a random position, as might be the case with other embodiments of the invention. Now, when one wishes to use the brush for brushing, the handle cover is merely pushed forward, so that the screw 138 engages the opposite end of the slot 136. This position is shown in FIG. 7. Here, it will be seen that the passage 124 has been effectively sealed off by contact with the interior of the brush handle. Also, the tubular member 122 has forced check valve 134 into its open position. Now, there is no pumping action but instead there is only the alternate suction and pressure on the pistons. Of course, there is some slight leakage past the pistons but this small amount of leakage does not interfere with the operation of the brush, and, also, because of the potential flushing action, it is not important if a small amount of saliva should lodge behind the pistons.

Figure 8:
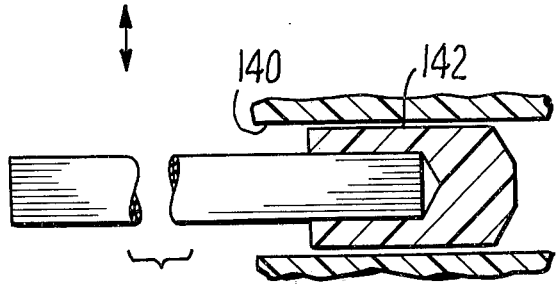
FIG. 8 is an enlarged view of a piston and brush wherein the piston is not provided with a ring.

The "leaky" pistons can take a variety of forms. In FIG. 8, a simple piston is shown wherein the cylinder wall 140 and the piston wall 142 have been fabricated to allow a small gap, but not provided with any form of sealing ring.

Figure 9:
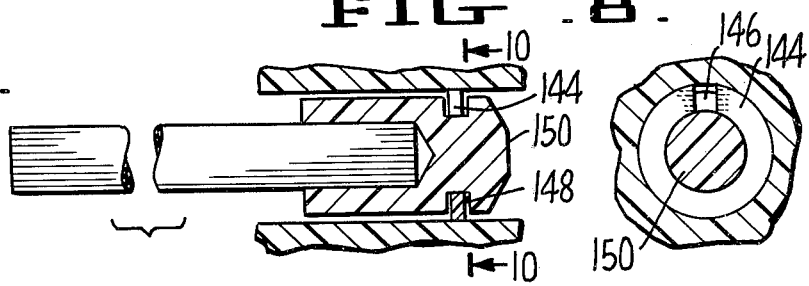
FIG. 9 is a similar view showing a piston with a split ring.
Figure 10:
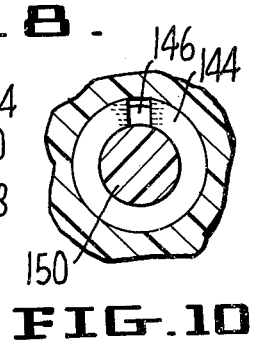
FIG. 10 shows a split ring suitable for use in the structure of FIG. 9.

In FIGS. 9 and 10 another structure is shown wherein the piston is provided with a split ring as is common with internal combustion engines. Thus, ring 144 has a split 146 therein for easy assembling. The ring fits in a ring groove 148 in piston 150.

This embodiment of the invention is equally applicable to brushes having two or even more heads such as the one described in FIG. 3.

The brush of this embodiment is relatively inexpensive to make since precision tolerances are not required of many of the parts and it also offers the advantage of providing an easy means of cleaning out the brush head and insuring that the bristles will always stop in the extended position.

Normally, the driving fluid for the brush of the present invention would be air, but any fluid, including a liquid, can be employed in the various mechanisms shown. Or, the drive means may be purely mechanical, such as vibrating rods, strings or reciprocating cams and gears. With a mechanical drive, the tufts may be spring-mounted or mounted in a pliable material to permit them to perform the desired adaption for irregularities in the teeth and gums.

Although certain specific embodiments of my invention have been described, it will be obvious to those skilled in the art that many variations can be made in the exact structure shown without departing from the spirit of this invention.

I claim:

1. A mechanical brush having a head with a plurality of tufts in said head, wherein each tuft is attached to an individual piston and said pistons are each mounted for individual reciprocating motion within said head, and means for powering said reciprocating motion internally within said head, independent of any tuft movement caused by tuft contact with an external object.

2. The structure of claim 1 wherein said means for powering said reciprocating motion comprises means for providing alternating suction and pressure behind said pistons.

3. The structure of claim 2 wherein said means for powering is pneumatic.

4. The structure of claim 3 having spring return means for said pistons.

5. The structure of claim 3 having a pneumatic chamber connected to said means for powering and having means for varying the volume of said chamber whereby the force exerted by the pistons can be varied.

6. The structure of claim 2 wherein said means for powering is hydraulic.

7. The structure of claim 2 having a diaphragm or bladder isolation means between said pistons and said means for powering said reciprocation whereby pressure and or suction is transmitted through said isolation means while maintaining a hermetic seal between the pistons and said means for powering said reciprocation.

8. The structure of claim 7 wherein said diaphragm or bladder isolation means prevents direct fluid communication between said head pistons and said means for powering and having additionally means for flushing the inside of said head and/or handle.

* * * * *

UNITED STATES PATENT AND TRADEMARK OFFICE
CERTIFICATE OF CORRECTION

PATENT NO. : 4,346,492
DATED : August 31, 1982
INVENTOR(S) : Terry S. Solow

It is certified that error appears in the above-identified patent and that said Letters Patent is hereby corrected as shown below:

The term of this patent subsequent to September 23, 1997, has been disclaimed.

Signed and Sealed this

Sixth Day of September 1983

[SEAL]

Attest:

GERALD J. MOSSINGHOFF

Attesting Officer

Commissioner of Patents and Trademarks